(12) United States Patent
Mine

(10) Patent No.: US 7,227,044 B2
(45) Date of Patent: Jun. 5, 2007

(54) CYCLOALKANONE COMPOSITION

(75) Inventor: Koji Mine, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/076,912

(22) Filed: Mar. 11, 2005

(65) Prior Publication Data

US 2005/0227909 A1  Oct. 13, 2005

(30) Foreign Application Priority Data

Mar. 15, 2004 (JP) ............................ 2004-072253

(51) Int. Cl.
*C07C 45/00* (2006.01)
*C07C 69/74* (2006.01)

(52) U.S. Cl. ...................... 568/343; 568/345; 568/353; 568/379; 560/122

(58) Field of Classification Search ..................... None
See application file for complete search history.

(56) References Cited

U.S. PATENT DOCUMENTS

| 4,260,830 | A |   | 4/1981 | Wilson et al. | ............... | 568/485 |
| 4,310,701 | A |   | 1/1982 | Wilson et al. | ............... | 568/347 |
| 4,668,827 | A |   | 5/1987 | Tamura et al. | ............... | 568/345 |
| 6,500,990 | B2 | * | 12/2002 | Asada et al. | ................. | 568/341 |
| 6,833,481 | B2 | * | 12/2004 | Yamamoto et al. | ......... | 568/341 |

FOREIGN PATENT DOCUMENTS

| DE | 134 274     |    | 9/1929  |
| EP | 0 033 604 A1 |   | 8/1981  |
| EP | 1 316 541 A1 |   | 6/2003  |
| EP | 1 433 773 A1 |   | 6/2004  |
| JP | 56-147740   |    | 11/1981 |
| JP | 2001-335529 |    | 12/2001 |

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

The present invention relates to a cycloalkanone composition which contains cycloalkanone (1) in an amount of 70 wt % or more based on the composition, wherein the content of a dimer of a cycloalkanone represented by formula (2) is 0.055 or less in terms of weight ratio to the cycloalkanone (1), a process for producing the same, a process for producing a composition containing alkyl acetate (5) by using the cycloalkanone composition, and an alkyl acetate composition obtained by the process

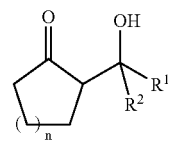

(1)

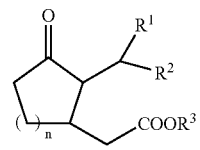

(5)

wherein n is an integer of 1 or 2, $R^1$ and $R^2$ each represent H, a C1 to C8 alkyl group etc., and $R^3$ represents a C1 to C3 alkyl group.

7 Claims, No Drawings

CYCLOALKANONE COMPOSITION

FIELD OF THE INVENTION

The present invention relates to a cycloalkanone composition useful for example as a synthetic intermediate of a physiologically active substance and perfume, a process for producing the same, an alkyl acetate composition using the same, which is useful for example as a perfume material and a physiologically active substance, and a process for producing the same.

BACKGROUND OF THE INVENTION

A process for producing 2-(1-hydroxyalkyl)cycloalkanone by aldol condensation of a cycloalkanone with an aldehyde or ketone in the presence of water and a basic catalyst is conventionally known as disclosed in JP-A 56-147740 and JP-A 2001-335529.

SUMMARY OF THE INVENTION

The present invention provides a cycloalkanone composition, which contains a cycloalkanone represented by formula (1) (referred to hereinafter as cycloalkanone (1)) in an amount of 70 wt % or more based on the composition, wherein the content of a dimer of a cycloalkanone represented by formula (2) is 0.055 or less in terms of weight ratio to the cycloalkanone (1),

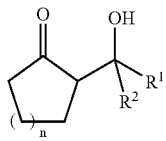
(1)

wherein n is an integer of 1 or 2, $R^1$ and $R^2$ independently represent a hydrogen atom, a C1 to C8 linear or branched alkyl group or a substituted or unsubstituted aryl group.

Further, the present invention provides a process for producing a cycloalkanone composition, including the step of reacting a cycloalkanone represented by formula (2) (referred to hereinafter as cycloalkanone (2)) with an aldehyde or ketone represented by formula (3) (referred to hereinafter as compound (3)) by aldol condensation in the presence of water and a basic catalyst at a mole ratio of water/compound of formula (3) of 1.5/1 to 5.5/1 to produce a cycloalkanone composition containing (1),

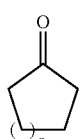
(2)

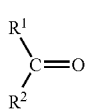
(3)

wherein n, $R^1$ and $R^2$ each has the same meaning as defined above.

Further, the present invention provides a process for producing an alkyl acetate composition containing an alkyl acetate represented by formula (5) (referred to hereinafter as alkyl acetate (5)):

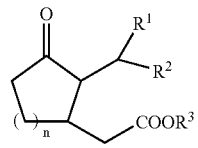
(5)

wherein n, $R^1$ and $R^2$ each have the same meaning as defined above, $R^3$ represents a C1 to C3 linear or branched alkyl group, which includes the steps of subjecting the cycloalkanone composition described above to a dehydration reaction, then subjecting the product to an isomerization reaction, then reacting the product with a malonic diester represented by formula (4) (referred to hereinafter as malonic diester (4)):

$$\begin{array}{c} COOR^3 \\ | \\ CH_2 \\ | \\ COOR^3 \end{array} \qquad (4)$$

wherein $R^3$ has the same meaning as defined above, and two $R^3$s may be the same as or different from each other, and reacting the product with water.

The invention also provides for an alkyl acetate composition obtained by the process described above.

DETAILED DESCRIPTION OF THE INVENTION

During the aldol condensation of a cycloalkanone with an aldehyde or ketone, a cycloalkanone dimer is produced as a byproduct, and this dimer has a boiling point near to that of cycloalkanones such as 2-(1-hydroxyalkyl or aryl) cycloalkanone and is thus hardly separated by distillation, and it was found that the dimer still remains in the final product alkyl(3-oxo-2-alkylcycloalkyl) acetate or alkyl (3-oxo-2-arylcycloalkyl) acetate, to cause a deterioration in quality, and the yield is lowered in rectification for removing the dimer. When the yield of cycloalkanones such as 2-(1-hydroxyalkyl or aryl) cycloalkanone is to be increased, the amount of the dimer produced as a byproduct is also inevitably increased.

The present invention provides a cycloalkanone composition containing cycloalkanones such as 2-(1-hydroxyalkyl or aryl) cycloalkanone in high purity with a reduced content of cycloalkanone dimers, a process for producing the same, a high-quality alkyl acetate composition using the same, which is useful for example as a perfume material and a physiologically active substance, and a process for efficiently producing the same.

The present inventors have found that when the reaction in aldol condensation is carried out under the control of the amount of water within a specified range relative to an aldehyde and/or a ketone, a cycloalkanone composition with a reduced content of cycloalkanone dimers can be obtained in high purity, thus improving the qualities of the final product alkyl acetate composition and simultaneously increasing the yield in rectification.

According to the present invention, a cycloalkanone composition with less formation of cycloalkanone dimers can be obtained in high purity, thus improving the qualities of the final product alkyl acetate composition and increasing the yield in rectification.

[Cycloalkanone Composition and the Process for Producing the Same]

The content of a dimer of cycloalkanone of formula (2) in the cycloalkanone composition of the present invention is 0.055 or less, more preferably 0.050 or less, in terms of weight ratio to cycloalkanone (1), from the viewpoint of serving as a perfume material excellent in quality and a starting material of physiologically active substance.

The content of the cycloalkanone (1) in the cycloalkanone composition of the present invention is 70 wt % or more, preferably 75 wt % or more, more preferably 80 wt % or more.

In the present invention, liquid chromatography, gas chromatography etc. are mentioned as the preferred methods of quantifying the cycloalkanone dimer and the cycloalkanone (1).

The cycloalkanone (1) is preferably one or more members selected from the group consisting of 2-(1-hydroxyalkyl)cycloalkanone and 2-(1-hydroxyaryl)cycloalkanone.

The content of cycloalkanone dimers as substances causing an offensive smell is low in the cycloalkanone composition of the present invention, and thus this composition can be used as a starting material to produce an alkyl acetate composition, excellent in quality and useful as a perfume material and a physiologically active substance.

To produce the cycloalkanone composition in the present invention, the reaction for aldol condensation of the cycloalkanone (2) with compound (3) in the presence of water and a basic catalyst is carried out under the control of the amount of water in a specific range.

From the viewpoint of attaining a good yield and suppressing formation of cycloalkanone dimers, the amount of water being present is determined to have a molar ratio of water/compound (3) of 1.5/1 to 5.5/1, preferably 2.5/1 to 5.5/1, even more preferably 3.0/1 to 5.0/1.

From the viewpoint of attaining a good yield and suppressing formation of cycloalkanone dimers, the amount of water being present may be preferably specified at a weight ratio of water/cycloalkanone (2) of 0.1/1 to 0.5/1, more preferably 0.15/1 to 0.5/1, even more preferably 0.15/1 to 0.38/1.

The cycloalkanone (2) used in the present invention is cyclopentanone or cyclohexanone, preferably cyclopentanone. Compound (3) is preferably a compound wherein $R^1$ is a C1 to C8 alkyl group or an aryl group and $R^2$ is a hydrogen atom, more preferably a compound wherein $R^1$ is a C1 to C8 alkyl group and $R^2$ is a hydrogen atom, even more preferably a compound wherein $R^1$ is a C3 to C5 alkyl group and $R^2$ is a hydrogen atom, and even more preferably an aldehyde (valeraldehyde) having a C4 linear alkyl group.

From the viewpoint of attaining a good yield, the molar ratio of the cycloalkanone (2) to compound (3), that is, the cycloalkanone (2)/compound (3), is preferably 1/1 or more, more preferably 1.2/1 to 4.0/1, even more preferably 1.2/1 to 3.0/1, even more preferably 1.5/1 to 2.7/1, in consideration of productivity such as recovery of an excess of cycloalkanone. By recovering an excess of cycloalkanone (2) by distillation etc., the cycloalkanone (2) can be efficiently used, and the cycloalkanone (1) can be increased to the desired purity.

From the viewpoint of securing a sufficient reaction rate and yield, the amount of the basic catalyst used is usually preferably 0.001 to 0.06 mol, more preferably 0.001 to 0.05 mol, per mol of compound (3).

The basic catalyst used in the present invention is preferably a compound represented by formula (6):

$$M(OH)_m \qquad (6)$$

wherein M is an alkali metal such as Li, Na, K etc. or an alkaline earth metal such as Mg, Ca, Ba etc., preferably an alkali metal, and m is an integer of 1 or 2.

The reaction temperature for aldol condensation is preferably −5 to 40° C., more preferably −5 to 30° C., from the viewpoint of prevention of coagulation of the aqueous layer and suppression of formation of cycloalkanone dimers etc.

For production of the cycloalkanone composition of the present invention, it is preferable that the cycloalkanone (2), water and a basic catalyst are introduced into a reaction bath, and while the mixture is regulated at the reaction temperature described above, compound (3) is added dropwise to the mixture. The time of dropwise addition may be changed depending on the temperature control ability of the reaction bath and does not affect the yield. After the dropwise addition is finished, an aging reaction may be carried out if necessary in order to increase the degree of conversion. The aging time is not particularly limited either, and as the aging time is increased, byproducts are gradually increased. In consideration of productivity, it is preferable that the time of dropwise addition of compound (3) is about 1 to 8 hours, and the aging time is about 1 to 6 hours. This reaction is conducted preferably in an inert gas atmosphere. The inert gas includes nitrogen, argon etc.

The pressure in the aldol condensation reaction, in terms of absolute pressure, is preferably 10 kPa to 1 MPa, more preferably 50 to 300 kPa, even more preferably 80 to 120 kPa.

The aldol condensation reaction is a reaction in a system of 2 layers, that is, cycloalkanone (2) and water, and thus a solvent destroying this system is not preferable. The solvent used in the present invention is not particularly limited insofar as it is inert to the reaction system, and does not hinder the separation and purification of the product, and examples include solvents having a boiling point in the range of about 140 to 210° C., such as aromatic hydrocarbon solvents (benzene, toluene etc.), aliphatic hydrocarbon solvents (nonane, decane, undecane etc.) etc.

Because the aqueous layer used in the aldol condensation reaction contains a large amount of cycloalkanone (2), the aqueous layer is desirably separated and repeatedly used. A part of the aqueous layer is partitioned into the oil layer so that when the aqueous layer is reused in the reaction, water and the basic catalyst in such a partitioned amount may be added to the aqueous layer. If necessary, water and the basic catalyst may be further added.

In the presence of the basic catalyst, layer separation is sometimes time-consuming. In this case, the reaction mixture is adjusted with an acid to a pH at which layer separation easily occurs, and the separated layer can be reused. When recovery of cycloalkanone (2) by distillation from the oil phase is also necessary after layer separation, the pH is adjusted desirably to the acidic side, preferably pH 4–7, in order to suppress the decomposition of cycloalkanone (1).

The acid used herein is not particularly limited, and general organic acids and inorganic acids can be used, among which sulfuric acid, phosphoric acid and condensed phosphoric acid are preferable for easy handling, price etc.

When the acid is added, it is preferable to add a basic catalyst in such an amount so as to change the pH value of the aqueous layer from neutral to the alkaline range (pH 7 or more), in addition to the basic catalyst in the above-mentioned amount so that the aqueous layer may be re-used for the reaction.

[Alkyl Acetate Composition and the Process for Producing the Same]

The composition containing alkyl acetate (5), useful for example as a perfume material and a physiologically active substance, can be obtained from the cycloalkanone composition of the present invention, according to a method described in, for example, JP-A 56-147740.

Specifically, the cycloalkanone composition containing (1) is subjected to a dehydration reaction with oxalic acid etc. to give a compound represented by formula (7):

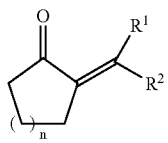

(7)

wherein n, $R^1$ and $R^2$ each have the meaning as defined above, followed by the isomerization reaction of the compound in the presence of an aqueous acid (hydrochloric acid, hydrobromic acid or the like) in n-butanol under reflux to give a compound represented by formula (8) (referred to hereinafter as compound (8)):

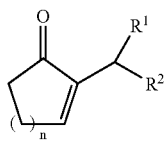

(8)

wherein n, $R^1$ and $R^2$ each have the meaning as defined above. Then, compound (8) is reacted with malonic diester (4) in the presence of a basic catalyst to give a compound represented by formula (9) (referred to hereinafter as compound (9)):

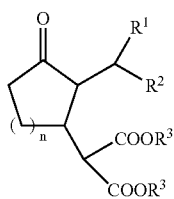

(9)

wherein n, $R^1$ and $R^2$ each have the meaning as defined above.

The malonic diester (4) is reacted with compound (8), preferably at a molar ratio (4)/(8) of 1/1 to 5/1, more preferably 1.2/1 to 2/1.

The basic catalyst includes alkali metals such as sodium, potassium etc. and alkali metal alkoxides such as sodium alkoxide, potassium alkoxide etc. The amount of the catalyst used is preferably 0.005 to 0.2 mol based on compound (8). The solvent is preferably a polar solvent such as alcohol etc. The reaction temperature is preferably in the range of −10 to 30° C., more preferably in the range of 0 to 20° C.

Then, the resulting compound (9) can be reacted with water to produce the alkyl acetate composition containing (5). The water may be added dropwise to the reaction system to react with compound (9), preferably at a molar ratio of water/(9) of 1/1 to 3/1. The reaction temperature is preferably in the range of 150 to 250° C.

The alkyl acetate composition containing (5) obtained by the process for the present invention has a lower content of cycloalkanone dimers, thus suppressing an offensive smell, and is useful for example as a perfume material and a physiologically active substance.

EXAMPLE

Next, examples according to the present invention will be explained. These examples are intended to describe preferred embodiments of the present invention and are not intended to be limiting of the invention.

Example 1

134.9 g (1.6 mols) of cyclopentanone, 27.1 g (1.5 mols) of water and 2.6 g (0.031 mol) of 48% NaOH were introduced into a 500-ml four-necked flask and cooled to 5° C. while stirring, and at the same temperature, 61.0 g (0.71 mol) of valeraldehyde was added dropwise thereto over 5 hours. After this dropwise addition was finished, the mixture was stirred at the same temperature for 2 hours. After the reaction was finished, the reaction mixture was neutralized with 2.5 g of 105% phosphoric acid, and the unreacted cyclopentanone was recovered by distillation from the organic layer, and the bottoms were analyzed by gas chromatography. The analysis was conducted by a methyl silicon column with diethylene glycol monoethyl ether (Carbitol) added as a standard substance. As a result, it was found that 86.1 g (0.51 mol) of 2-(1-hydroxy-n-pentyl)cyclopentanone, 2.8 g (0.018 mol) of pentylidene cyclopentanone and 2.6 g (0.016 mol) of 2-(1-hydroxy-cyclopentyl)cyclopentanone were contained in the reaction product.

Example 2

134.8 g (1.6 mols) of cyclopentanone, 47.2 g (2.6 mols) of water and 1.6 g (0.019 mol) of 48% NaOH were introduced into a 500-ml four-necked flask and cooled to 15° C. while stirring, and at the same temperature, 61.7 g (0.72 mol) of valeraldehyde was added dropwise thereto over 5 hours. After this dropwise addition was finished, the mixture was stirred at the same temperature for 1.5 hours. After the reaction was finished, the reaction mixture was neutralized with 1.5 g of 105% phosphoric acid, and the bottoms after distillation in the same manner as in Example 1 were analyzed by gas chromatography. As a result, it was found that 106.1 g (0.62 mol) of 2-(1-hydroxy-n-pentyl)cyclopentanone, 3.2 g (0.021 mol) of pentylidene cyclopentanone and 5.1 g (0.030 mol) of 2-(1-hydroxy-cyclopentyl)cyclopentanone were contained in the reaction product.

Example 3

199.4 g (2.4 mols) of cyclopentanone, 59.9 g (3.3 mols) of water and 1.2 g (0.014 mol) of 48% NaOH were introduced into a 500-ml four-necked flask and cooled to 15° C. while stirring, and at the same temperature, 60.1 g (0.70 mol) of valeraldehyde was added dropwise thereto over 5 hours. After this dropwise addition was finished, the mixture was stirred at the same temperature for 2 hours. After the reaction was finished, the reaction mixture was neutralized with 1.1 g of 105% phosphoric acid, and the bottoms after distillation in the same manner as in Example 1 was analyzed by gas chromatography. As a result, it was found that 107.2 g (0.63 mol) of 2-(1-hydroxy-n-pentyl)cyclopentanone, 2.0 g (0.013 mol) of pentylidene cyclopentanone and 5.3 g (0.032 mol) of 2-(1-hydroxy-cyclopentyl)cyclopentanone were contained in the reaction product.

Example 4

151.7 g (1.8 mols) of cyclopentanone, 27.1 g (1.5 mols) of water and 0.60 g (0.007 mol) of 48% NaOH were introduced into a 500-ml four-necked flask and cooled to 15° C. while stirring, and at the same temperature, 70.2 g (0.82 mol) of valeraldehyde was added dropwise thereto over 3 hours. After this dropwise addition was finished, the mixture was stirred at the same temperature for 4 hours. After the reaction was finished, the reaction mixture was neutralized with 0.6 g of 105% phosphoric acid, and the bottoms after distillation in the same manner as in Example 1 was analyzed by gas chromatography. As a result, it was found that 104.0 g (0.61 mol) of 2-(1-hydroxy-n-pentyl)cyclopentanone, 1.3 g (0.009 mol) of pentylidene cyclopentanone and 1.0 g (0.006 mol) of 2-(1-hydroxy-cyclopentyl)cyclopentanone were contained in the reaction product.

Example 5

117.8 g (1.4 mols) of cyclopentanone, 62.5 g (3.5 mols) of water and 1.4 g (0.016 mol) of 48% NaOH were introduced into a 500-ml four-necked flask and cooled to 15° C. while stirring, and at the same temperature, 68.6 g (0.80 mol) of valeraldehyde was added dropwise thereto over 4 hours. After this dropwise addition was finished, the mixture was stirred at the same temperature for 4 hours. After the reaction was finished, the reaction mixture was neutralized with 1.4 g of 105% phosphoric acid, and the bottoms after distillation in the same manner as in Example 1 was analyzed by gas chromatography. As a result, it was found that 114.2 g (0.67 mol) of 2-(1-hydroxy-n-pentyl)cyclopentanone, 3.7 g (0.024 mol) of pentylidene cyclopentanone and 3.5 g (0.021 mol) of 2-(1-hydroxy-cyclopentyl)cyclopentanone were contained in the reaction product.

Comparative Example 1

718.9 g (8.6 mols) of cyclopentanone, 378.6 g (21.0 mols) of water and 8.6 g (0.10 mol) of 48% NaOH were introduced into a 2000-ml four-necked flask and cooled to 15° C. while stirring, and at the same temperature, 320.0 g (3.7 mols) of valeraldehyde was added dropwise thereto over 5 hours. After this dropwise addition was finished, the mixture was stirred at the same temperature for 1 hour. After the reaction was finished, the reaction mixture was neutralized with 8.6 g of 105% phosphoric acid, and the bottoms after distillation in the same manner as in Example 1 was analyzed by gas chromatography. As a result, it was found that 551.3 g (3.2 mols) of 2-(1-hydroxy-n-pentyl)cyclopentanone, 23.0 g (0.15 mol) of pentylidene cyclopentanone and 32.5 g (0.19 mol) of 2-(1-hydroxy-cyclopentyl)cyclopentanone were contained in the reaction product.

The reaction conditions and the results in Examples 1 to 5 and Comparative Example 1 are collectively shown in Table 1.

TABLE 1

| | | Example | | | | | Comparative Example |
|---|---|---|---|---|---|---|---|
| | | 1 | 2 | 3 | 4 | 5 | 1 |
| Reaction conditions | Reaction temperature (° C.) | 5 | 15 | 15 | 15 | 15 | 15 |
| | Dropping time of compound of formula (3) (hours) | 5 | 5 | 5 | 3 | 4 | 5 |
| | Aging time (hours) | 2 | 1.5 | 2 | 4 | 4 | 1 |
| | water/compound of formula (3) (molar ratio) | 2.23 | 3.72 | 4.81 | 1.87 | 4.41 | 5.73 |
| | water/cycloalkanone of formula (2) (weight ratio) | 0.211 | 0.356 | 0.303 | 0.181 | 0.537 | 0.533 |
| | cycloalkanone of formula (2)/compound of fomula (3) (molar ratio) | 2.26 | 2.24 | 3.40 | 2.21 | 1.76 | 2.30 |
| Results | cycloalkanone diamer/cycloalkanone(1) (weight ratio) | 0.030 | 0.048 | 0.050 | 0.010 | 0.031 | 0.059 |
| | Reaction yield of cycloalkanone(1)*[1] (%) | 71.4 | 87.0 | 90.2 | 74.9 | 84.2 | 87.2 |
| | Purity of cycloalkanone(1)-containing compound*[2] (weight-%) | 78.5 | 89.0 | 87.4 | 83.4 | 86.2 | 85.7 |

*[1]Reaction yield of cycloalkanone (1) = [cycloalkanone (1) (mol)/compound of formula (3) (mol)] × 100
*[2]Content of cycloalkanone (1) in the organic layer after recovery by distillation

Example 6

112.3 g (1.3 mols) of cyclopentanone, 50.0 g (2.8 mols) of water and 0.53 g (0.0064 mol) of 48% NaOH were introduced into a 500-ml four-necked flask and cooled to 15° C. while stirring, and at the same temperature, 50.0 g (0.58 mol) of valeraldehyde was added dropwise thereto over 5 hours. After this dropwise addition was finished, the mixture was stirred at the same temperature for 2 hours. After the reaction was finished, the reaction mixture was neutralized with 0.53 g of 105% phosphoric acid, and the bottoms after distillation in the same manner as in Example 1 was analyzed by gas chromatography. As a result, it was found that 84.4 g (0.50 mol) of 2-(1-hydroxy-n-pentyl)cyclopentanone, 1.3 g (0.0088 mol) of pentylidene cyclopentanone and 2.5 g (0.015 mol) of 2-(1-hydroxy-cyclopentyl)cyclopentanone were contained in the reaction product (cycloalkanone dimer/cycloalkanone (1) (weight ratio)=0.030; the content of the cycloalkanone (1) in the organic layer after recovery by distillation was 84.4 wt %).

This reaction was conducted further twice, and the product was distilled to recover cyclopentanones and water. And 0.0204 mol of oxalic acid was added to 1.0 mol of 2-(1-hydroxy-n-pentyl)cyclopentanone and 0.018 mol of pentylidene cyclopenanone contained in the bottoms after distillation, and then this mixture reacted at 120° C. The amount of 2-pentylidene cyclopentanone contained in the reaction mixture was 142 g (0.94 mol). A material obtained after filtrating this reaction mixture was dissolved in 153 g n-butanol and heated to 130° C., and a mixture of 14.5 g (0.15 mol) of 3-picoline and 10.5 g (0.1 mol) of 35% hydrochloric acid was added dropwise thereto over 30 minutes. After the dropwise addition, the reaction mixture was stirred under heating at the same temperature for 3.5 hours. After the reaction was finished, the reaction mixture was cooled to room temperature and neutralized with an aqueous solution of sodium hydroxide, and as a result of analysis of the organic layer, it was found that 118 g of 2-pentyl-2-cyclopentenone was contained in the reaction product. The yield in this isomerization reaction was 83%.

From this reaction product, 95 g (0.6 mol) of 2-pentyl-2-cyclopentenone was purified. This product (95 g (0.6 mol) of 2-pentyl-2-cyclopentenone) was added dropwise at 0° C. for 2 hours to a mixture obtained by dissolving 118 g (0.9 mol) of dimethyl malonate in 38 g anhydrous methanol in a nitrogen atmosphere, cooling the solution to 0° C., and adding 6.5 g (0.036 mol) of sodium methoxide (30% methanol solution) thereto. After the dropwise addition was finished, the mixture was stirred at the same temperature for 3 hours. Unreacted dimethyl malonate was distilled away under reduced pressure, whereby 160 g Michael addition product was obtained.

A reactor equipped with a distillation effluent tube was charged with the Michael addition product obtained above and heated to 215° C., and water was added dropwise at a rate of 3.2 g/h (2%/h). While generated carbon dioxide and methanol were distilled away, the reaction was carried out at 215° C. for 4 hours under dropping. After the reaction was finished, 123 g of methyl 3-oxo-2-pentylcyclopentylacetate was obtained in 126 g crude product.

Methyl 3-oxo-2-pentylcyclopentylacetate obtained by rectification of the crude product contained 2-(1-hydroxy-cyclopentyl) cyclopentanone at a very low level of 11 ppm, and had a fruity and jasmine-like fragrance, and was excellent as a perfume material.

The invention claimed is:

1. A process for producing a cycloalkanone composition comprising a cycloalkanone represented by formula (1) in an amount of 70 wt % or more based on the composition, wherein the content of a dimer of a cycloalkanone represented by formula (2) is 0.055 or less in terms of weight ratio to the cycloalkanone (1),

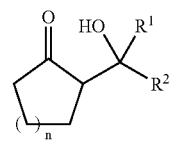
(1)

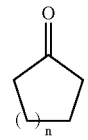
(2)

in which said process comprises:
reacting the cycloalkanone represented by formula (2) with an aldehyde or ketone represented by formula (3) by aldol condensation in the presence of water and a basic catalyst at a mole ratio of water/compound of formula (3) of 1.5/1 to 5.5/1,

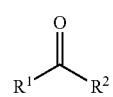
(3)

wherein n is an integer of 1 or 2, $R^1$ and $R^2$ independently represent a hydrogen atom, a C1 to C8 linear or branced alkyl grou or a substituted or unsubstituted aryl group.

2. The process according to claim 1, wherein water is present at a weight ratio of water/cycloalkanone of formula (2) of 0.1/1 to 0.5/1.

3. The process according to claim 1 or 2, wherein the cycloalkanone of formula (2) is reacted with compound of formula (3) at a mole ratio of (2)/(3) of 1.2/1 to 4.0/1.

4. A process for producing an alkyl acetate composition comprising an alkyl acetate represented by formula (5):

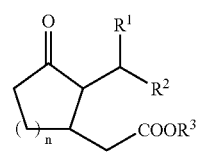
(5)

wherein n is an integer of 1 or 2, $R^1$ and $R^2$ independently represent a hydrogen atom, a C1 to C8 linear or branched alkyl group or a substituted or unsubstituted aryl group, and $R^3$ represents a C1 to C3 linear or branched alkyl group, in which said process comprises:
subjecting a cycloalkanone composition to a dehydration reaction to obtain a product composition,
wherein the cycloalkanone composition comprises a cycloalkanone represented by formula (1) in an amount of 70 wt % or more based on the composition, wherein the content of a dimer of a cycloalkanone represented by formula (2) is 0.055 or less in terms of weight ratio to the cycloalkanone (1),

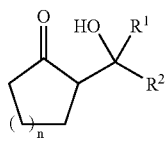 (1)

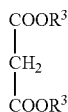 (2)

then subjecting the product composition to an isomerization reaction in order to obtain an isomerization product, then reacting the isomerization product with a malonic diester represented by formula (4) in order to obtain a product:

$$\begin{array}{c} COOR^3 \\ | \\ CH_2 \\ | \\ COOR^3 \end{array} \quad (4)$$

wherein $R^3$ has the same meaning as defined above and two $R^3$s maybe the same as or different from each other, and reacting the product with water.

5. The process according to claim 4, wherein the alkyl acetate represented by formula (5) is at least one alkyl acetate selected from the group consisting of alkyl(3-oxo-2-alkylcycloalkyl) acetate and alkyl(3-oxo-2-arylcycloalkyl) acetate.

6. The process according to claim 1, wherein the cycloalkanone (1) is at least one cycloalkanone selected from the group consisting of 2-(1-hydroxyalkyl)cycloalkanone and 2-(1-hydroxyaryl)cycloalkanone.

7. The process according to claim 4, wherein the cycloalkanone (1) is at least one cycloalkanone selected from the group consisting of 2-(1-hydroxyalkyl)cycloalkanone and 2-(1-hydroxyaryl)cycloalkanone.

* * * * *